(12) United States Patent
Dace et al.

(10) Patent No.: US 12,186,914 B2
(45) Date of Patent: Jan. 7, 2025

(54) ROBOTIC ARM GUIDE AS A DEPTH STOP

(71) Applicant: MAZOR ROBOTICS, LTD., Caesarea (IL)

(72) Inventors: Mark C. Dace, Collierville, TN (US); Adam D. Glaser, Germantown, TN (US); Aviv Ellman, Kfar Sava (IL); Dany Junio, Netanya (IL); Elad Ratzabi, Beit Herut (IL); Gillan M. Grimberg, Tel Aviv-Jaffa (IL)

(73) Assignee: MAZOR ROBOTICS, LTD. (IL)

( * ) Notice: Subject to any disclaimer, the term of this patent is extended or adjusted under 35 U.S.C. 154(b) by 369 days.

(21) Appl. No.: 17/591,390

(22) Filed: Feb. 2, 2022

(65) Prior Publication Data

US 2023/0241775 A1    Aug. 3, 2023

(51) Int. Cl.
*B25J 9/16* (2006.01)
*A61B 34/00* (2016.01)
*A61B 34/10* (2016.01)
*A61B 34/20* (2016.01)

(52) U.S. Cl.
CPC .............. *B25J 9/1676* (2013.01); *A61B 34/10* (2016.02); *A61B 34/20* (2016.02); *A61B 34/70* (2016.02); *A61B 2034/2074* (2016.02)

(58) Field of Classification Search
CPC ......... A61B 34/10; A61B 34/20; A61B 34/70; A61B 2034/2074; A61B 2090/034; A61B 2090/061; A61B 2034/2046; A61B 34/32; A61B 90/03; A61B 34/30; A61B 2034/302; B25J 9/1676
See application file for complete search history.

(56) References Cited

U.S. PATENT DOCUMENTS 6,228,089 B1    5/2001  Wahrburg
2005/0096502 A1*  5/2005  Khalili ................... A61B 34/72
                                              600/129

(Continued)

FOREIGN PATENT DOCUMENTS

CA        2652245 A1 * 11/2007  ............. A61B 34/30
EP        3354223 A1 *  8/2018  ......... A61B 17/1615
WO   WO-2007114975 A2 * 10/2007  ......... A61B 1/00149

OTHER PUBLICATIONS

International Search Report and Written Opinion in Application No. PCT/IL2023/050089 dated May 19, 2023.

*Primary Examiner* — Kyle T Johnson
(74) *Attorney, Agent, or Firm* — FOX ROTHSCHILD LLP (57) ABSTRACT

Disclosed herein are systems and methods for a robotic arm guide used as a depth stop. For example, a system for positioning a surgical tool includes a surgical robotic system having a robot arm with a guide sleeve, the guide sleeve defining axial and lateral directions. The system is further configured to (i) receive a surgical plan associated with a subject, the surgical plan including three-dimensional pre-operative data related to the subject, (ii) determine, based on the surgical plan, a desired trajectory of a distal end of the surgical tool as the surgical tool is inserted into the guide sleeve, and (iii) transmit one or more control signals to the surgical robotic system, causing the surgical robotic system to orient and position the guide sleeve such that the distal end of the surgical tool follows the desired trajectory when the surgical tool is inserted in the guide sleeve.

17 Claims, 7 Drawing Sheets

(56) References Cited

U.S. PATENT DOCUMENTS

| | | | |
|---|---|---|---|
| 2011/0040305 A1* | 2/2011 | Gomez | A61B 34/74 |
| | | | 606/130 |
| 2011/0319941 A1* | 12/2011 | Bar | A61B 34/30 |
| | | | 606/279 |
| 2014/0142592 A1* | 5/2014 | Moon | A61B 34/37 |
| | | | 901/8 |
| 2014/0350614 A1* | 11/2014 | Frey | A61B 34/10 |
| | | | 606/86 R |
| 2015/0351860 A1* | 12/2015 | Piron | A61B 5/065 |
| | | | 600/417 |
| 2016/0030124 A1* | 2/2016 | Kishi | A61B 90/50 |
| | | | 600/102 |
| 2019/0231447 A1* | 8/2019 | Ebbitt | A61B 34/30 |
| 2020/0138518 A1* | 5/2020 | Lang | A61B 90/37 |
| 2020/0246025 A1* | 8/2020 | Akhlaghpour | A61B 34/20 |
| 2021/0001132 A1 | 4/2021 | Coiseur | |
| 2021/0113275 A1* | 4/2021 | Coiseur | A61B 34/20 |
| 2021/0121186 A1* | 4/2021 | Mincieli | A61B 90/06 |
| 2021/0001282 A1 | 5/2021 | Kang et al. | |
| 2021/0001973 A1 | 7/2021 | Li et al. | |
| 2021/0002597 A1 | 8/2021 | Varkut et al. | |
| 2023/0241775 A1* | 8/2023 | Dace | A61B 34/70 |
| | | | 700/255 |

\* cited by examiner

ROBOTIC ARM GUIDE AS A DEPTH STOP

FIELD

The present technology is generally related to systems and methods for robot-assisted surgery.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. Non-surgical treatments, such as medication, rehabilitation and exercise can be effective, however, may fail to relieve the symptoms associated with these disorders. Surgical treatment of these spinal disorders includes corrective fusion, fixation, discectomy, laminectomy and implantable prosthetics. As part of these surgical treatments, interbody devices can be employed with spinal constructs, which include implants such as bone fasteners and vertebral rods to provide stability to a treated region. These implants can redirect stresses away from a damaged or defective region while healing takes place to restore proper alignment and generally support the vertebral members. During surgical treatment, one or more rods and bone fasteners can be delivered to a surgical site. Surgical tools are employed, for example, to engage the fasteners for attachment to the exterior of two or more vertebral members. Robotic-assisted location of surgical tools has the potential to increase the accuracy of surgery and improve patient outcomes.

This document describes methods and systems that are directed to addressing the problems described above, and/or other issues.

SUMMARY

The techniques of this disclosure generally relate to a robotic arm guide used as a depth stop for surgical tools.

In one aspect, the present disclosure provides a system for positioning a surgical tool. The system includes a surgical robotic system having a robot arm, the robot arm having a guide sleeve defining axial and lateral directions. The system further includes one or more computer readable storage devices configured to store a plurality of computer executable instructions and one or more hardware computer processors in communication with the one or more computer readable storage devices and configured to execute the plurality of computer executable instructions. The computer executable instructions cause the system to receive a surgical plan associated with a subject, the surgical plan including three-dimensional preoperative data related to the subject. The computer executable instructions further cause the system to determine, based on the surgical plan, a desired trajectory of a distal end of the surgical tool as the surgical tool is inserted into the guide sleeve. The computer executable instructions further cause the system to determine, based on the surgical plan, a desired position of the distal end of the surgical tool. The computer executable instructions further cause the system to transmit one or more control signals to the surgical robotic system, causing the surgical robotic system to orient and position the guide sleeve based on one or more dimensions of the surgical tool and the desired trajectory and position of the distal end of the surgical tool, such that the distal end of the surgical tool follows the desired trajectory when the surgical tool is inserted in the guide sleeve and such that the distal end of the surgical tool achieves the desired position when the surgical tool is fully inserted in the guide sleeve.

Implementations of the disclosure may include one or more of the following optional features. In some examples, the plurality of computer executable instructions, when executed, further cause the system to transmit one or more second control signals to the surgical robotic system, causing the surgical robotic system to orient and position the guide sleeve based on one or more second dimensions of a second surgical tool. The surgical tool may be a burr and the second surgical tool is a bone graft delivery device. In some examples, the plurality of computer executable instructions, when executed, further cause the system to determine, based on the surgical plan, a second desired trajectory of a distal end of a second surgical tool as the second surgical tool is inserted into the guide sleeve. The plurality of computer executable instructions may further cause the system to determine, based on the surgical plan, a second desired position of the distal end of the second surgical tool; and transmit one or more second control signals to the surgical robotic system. In some examples, transmitting the one or more second control signals to the surgical robotic system causes the surgical robotic system to reorient and/or reposition the guide sleeve based on one or more second dimensions of the second surgical tool and the second desired trajectory and position, such that the distal end of the second surgical tool follows the second desired trajectory when the second surgical tool is inserted in the guide sleeve, and such that the distal end of the second surgical tool achieves the second desired position when the second surgical tool is fully inserted in the guide sleeve. The desired trajectory and the second desired trajectory may be different. The desired trajectory and the second desired trajectory may pass through the fascia of the subject at the same point.

In some examples, wherein the plurality of computer executable instructions, when executed, further cause the system to determine, based on the surgical plan, a plurality of additional desired positions of the distal end of the surgical tool, the plurality of additional desired positions defining a volume and transmit one or more additional control signals to the surgical robotic system. Transmitting the one or more additional control signals to the surgical robotic system may cause the surgical robotic system to orient and position the guide sleeve based on the one or more dimensions of the surgical tool and the plurality of additional desired positions of the distal end of the surgical tool, such that when the surgical tool is fully inserted in the guide sleeve, the distal end of the surgical tool achieves the plurality of additional desired positions. The robot arm may further include a cannula disposed within the guide sleeve, wherein the cannula is configured to receive the surgical tool. The surgical tool may include a flange and the guide sleeve may be configured to prevent the surgical tool from being inserted into the guide sleeve past the point where the flange contacts the proximal end of the guide sleeve.

In another aspect, the present disclosure provides a robotic system. The robotic system includes a robot arm having a guide sleeve defining axial and lateral directions and a surgical planning and execution system. The surgical planning and execution system is configured to determine a desired trajectory of a distal end of a surgical tool as the surgical tool is inserted into the guide sleeve. The surgical planning and execution system is further configured to determine on one or more dimensions of the surgical tool and determine a desired position of the distal end of the surgical tool. The surgical planning and execution system is further configured to cause the robot arm to orient and position the guide sleeve based on the one or more dimensions of the surgical tool and the desired trajectory and position of the distal end of the surgical tool, such that the distal end of the surgical tool follows the desired trajectory when the surgical tool is inserted in the guide sleeve, and such that the distal end of the surgical tool achieves the desired position when the surgical tool is fully inserted in the guide sleeve.

Implementations of the disclosure may include one or more of the following optional features. In some examples, the robot arm further includes a cannula disposed within the guide sleeve, wherein the cannula is configured to receive the surgical tool. The surgical tool may include a drill or burr.

In another aspect, the present disclosure provides a method of positioning a surgical tool. The method includes mounting a surgical robotic arm on a subject, the robotic arm including a guide sleeve, the guide sleeve defining axial and lateral directions. The method further includes receiving, from an electronic device, a surgical plan associated with the subject, the surgical plan including three-dimensional preoperative data related to the subject. The method further includes determining, based on the surgical plan, a desired trajectory of a distal end of the surgical tool as the surgical tool is inserted into the guide sleeve. The method further includes determining, based on the surgical plan, a desired position of the distal end of the surgical tool and transmitting one or more control signals to the robotic arm. Transmitting one or more control signals to the robotic arm causes the robotic arm to orient and position the guide sleeve based on one or more dimensions of the surgical tool and the desired trajectory and position of the distal end of the surgical tool, such that the distal end of the surgical tool follows the desired trajectory when the surgical tool is inserted in the guide sleeve, and such that the distal end of the surgical tool achieves the desired position when the surgical tool is fully inserted in the guide sleeve. The method further includes disposing the surgical tool within the guide sleeve such that the lateral position of the surgical tool is defined by the guide sleeve and an axial position of a distal end of the surgical tool is defined relative to an axial reference of the guide sleeve.

Implementations of the disclosure may include one or more of the following optional features. In some examples, the axial reference is the proximal end of the guide sleeve and the proximal end of the guide sleeve includes a depth stop. The desired position may be internal to the subject and the axial reference may be external to the subject. In some examples, the method further includes removing the surgical tool from the guide sleeve and disposing a second surgical tool within the guide sleeve. The method may further include reposition and/or reorienting the guide sleeve after removing the surgical tool and before disposing the second surgical tool within the guide sleeve. In some examples, the method further includes determining, based on the surgical plan, a second desired trajectory of a distal end of the second surgical tool as the second surgical tool is inserted into the guide sleeve. The desired trajectory of the distal end of the surgical tool may target a facet of a vertebra of the subject and the desired trajectory of the distal end of the second surgical tool may target a pedicle of the vertebra of the subject. The method may further include monitoring the position of the distal end of the surgical tool with a medical imaging system while disposing the surgical tool in the guide sleeve. In some examples, the method includes receiving three-dimensional preoperative data related to the subject and registering the subject position and orientation relative to the robotic arm based on the preoperative data.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other and are not necessarily "superior" and "inferior". Generally, similar spatial references of different aspects or components indicate similar spatial orientation and/or positioning, i.e., that each "first end" is situated on or directed towards the same end of the device. Further, the use of various spatial terminology herein should not be interpreted to limit the various insertion techniques or orientations of the implant relative to the positions in the spine.

The following terms shall have, for purposes of this application, the respective meanings set forth below:

A "computing device," "electronic device," or "computer" refers to a device or system that includes a processor and memory. Each device may have its own processor and/or memory, or the processor and/or memory may be shared with other devices as in a virtual machine or container arrangement. The memory will contain or receive programming instructions that, when executed by the processor, cause the electronic device to perform one or more operations according to the programming instructions. Examples of electronic devices include personal computers, servers, mainframes, virtual machines, containers, mobile electronic devices such as smartphones, Internet-connected wearables, tablet computers, laptop computers, and appliances and other devices that can communicate in an Internet-of-things arrangement. In a client-server arrangement, the client device and the server are electronic devices, in which the server contains instructions and/or data that the client device accesses via one or more communications links in one or more communications networks. In a virtual machine arrangement, a server may be an electronic device, and each virtual machine or container also may be considered an electronic device. In the discussion below, a client device, server device, virtual machine or container may be referred to simply as a "device" for brevity. Additional elements that may be included in electronic devices will be discussed below in the context of FIG. 4.

The terms "memory," "computer-readable medium" and "data store" each refer to a non-transitory device on which computer-readable data, programming instructions or both are stored. Unless the context specifically states that a single device is required or that multiple devices are required, the terms "memory," "computer-readable medium" and "data store" include both the singular and plural embodiments, as well as portions of such devices such as memory sectors.

Figure 1:
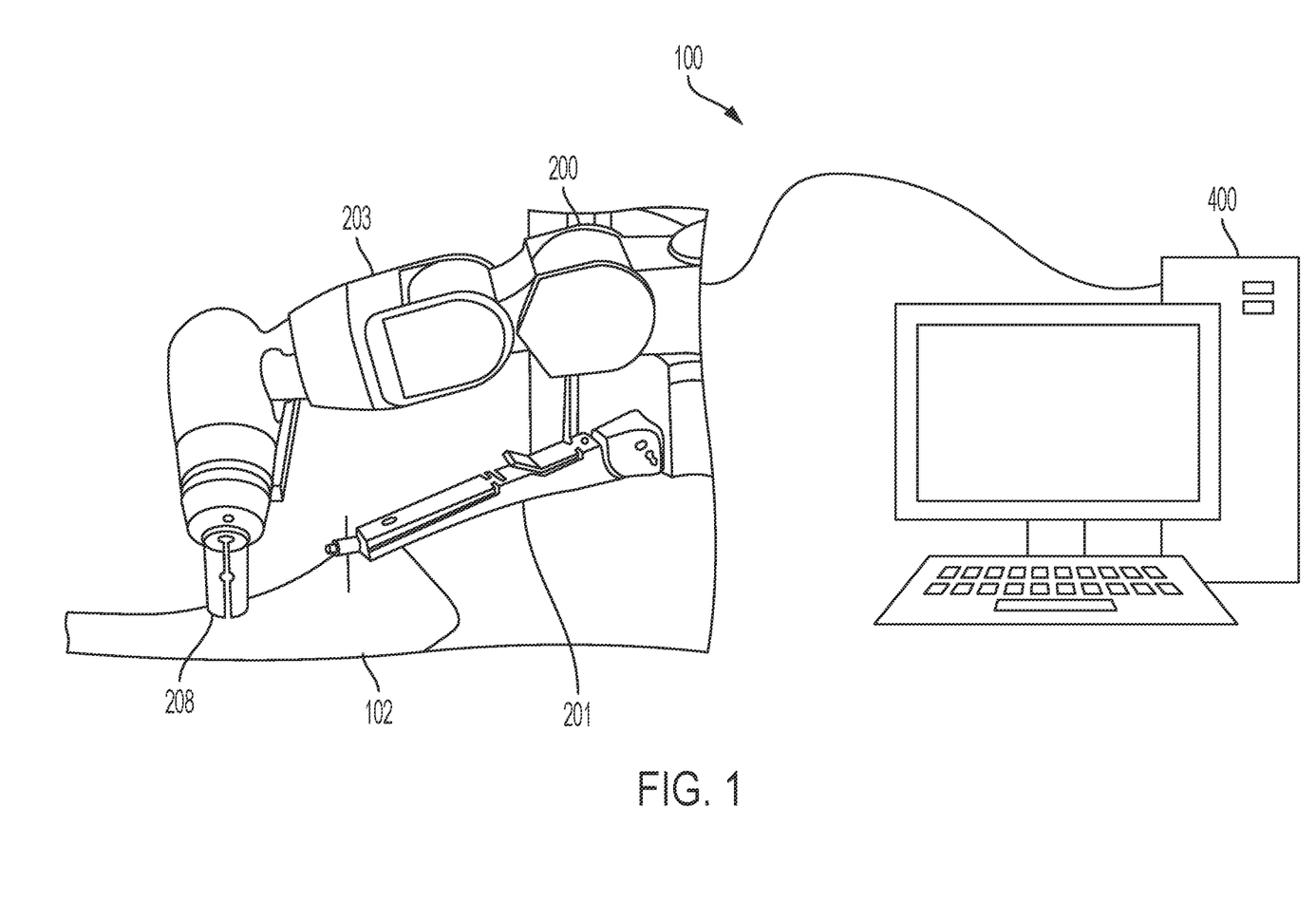
FIG. 1 illustrates an example environment for robot-assisted surgery.

The system(s) described in this disclosure are generally directed to systems and methods for robot-assisted surgery and in particular to robot-assisted spinal surgery. FIG. 1 shows an example environment 100 for performing robot-assisted spinal surgery. The environment 100 includes a subject 102 of the surgery. The subject 102 may have a spinal condition, such as stenosis, spondylolisthesis, a fracture, a deformity, a fracture, a tumor, and so forth. The condition may be treated using surgery, such as a spinal fusion. Spinal fusion includes using bone graft to cause two vertebrae to grow together into one bone. Spinal fusion may also include implanting spinal rods, plates, cages, and/or screws to help bones in the spine fuse together. Accurate positioning, on the spine of the subject 102, of spinal implants such as these increases positive surgical outcomes. In other cases, such as removing tumors near the spine, the surgery may include removing tumorous tissue and not removing healthy tissue. In these cases, accurate positioning of tissue-removing surgical tools 210 with respect to the subject 102 (and with respect to the spine of the subject 102) increases positive surgical outcomes.

The environment 100 may include a robotic system 200 to assist placement of surgical tools 210. The robotic system 200 may be rigidly mounted to a surface such as a floor or table of an operating room. Here, the robotic system 200 includes a robot arm 203 supporting a cylindrical guide sleeve 208 and has multiple joints configured to rotate and/or articulate, providing the arm 203 with multiple degrees of freedom. The environment 100 may also include a computing device 400, e.g., using the equipment shown in FIG. 4. The computing device 400 may include or have access to a data store containing medical records and/or medical images, such as x-rays, or the result of a Computed Tomography (CT) scan, or the like. The computing device 400 may also interface with the robotic system 200 through a wired or wireless communication channel, such as a computer communication network, and may be configured to transmit commands or signals through the communication channel to control movement of the robotic system 200. In some examples, the computing device 400 is configured to execute surgical planning and execution software. The surgical planning and execution software may include a surgical plan associated with the subject 102. The surgical plan may be developed prior to surgery and may be based on medical images, medical records, surgeon preferences, available surgical implants, prior outcomes or other subjects, and so forth.

Figure 2A:
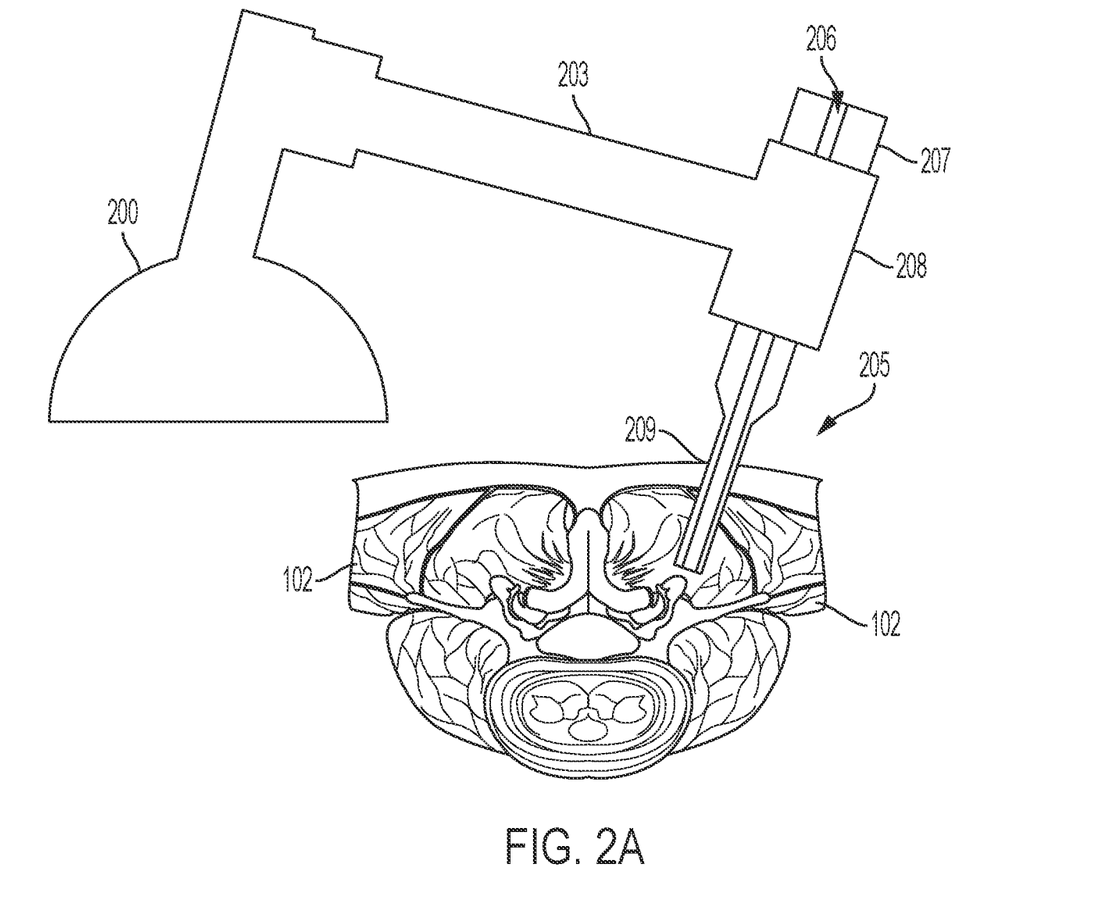
FIGS. 2A-2D illustrate an example robot system.

As shown in FIG. 2A, the robotic system 200 also includes a robot arm 203 supporting a cylindrical sleeve 208.

The sleeve 208 may be positioned and oriented by manipulating joints of the robotic system 200. The sleeve 208 may be used to guide or position surgical tools 210. In some examples, a computer-based surgical planning and execution system is configured to control the joints of the robotic system 200, e.g., operating the joints to position and orient the sleeve 208 according to a defined surgical plan. The surgical planning and execution system may develop the surgical plan based on medical record information related to the subject 102 and/or medical images, such as x-ray, CT scan, or magnetic resonance imaging (MM) scans of the subject 102 taken prior to the surgery. In some examples, the surgical planning and execution system applies a trained machine-learning model to the medical record information and/or medical images to determine the surgical plan prior to surgery. The surgical plan may include a model post-operative anatomical configuration of the subject 102 based on the medical record information and/or medical images and based on surgical outcomes of other patients (e.g., post-operative medical record information and/or medical images of other patients). The surgical planning and execution system may also be configured to receive sensor data during the surgical procedure from sensors attached to the subject 102 which measure or track the position and orientation of anatomical structures (such as the position and orientation of one or more vertebrae) of the subject 102, and/or the position of one or more surgical tools 210, and adjust the surgical plan in real-time based on the sensor data. Here, the robotic system 200 includes a second arm 201, the second arm 201 configured to detect the position of one or more vertebrae of the subject 102. In some examples, the robotic system 200 is configured to register the position of the subject 102 and to position and/or orient the sleeve 208 relative to the registered position of one or more vertebrae of the subject 102.

As shown in FIG. 2A, the robotic system 200 may position and orient the cylindrical sleeve 208 with respect to a surgical site 205 of the subject 102. The surgical site 205 is the general area of the subject 102 where the surgery takes place. In some examples, the surgical site 205 include a point of incision 209 through the skin or facia of the subject 102 through which surgical tools 210 and/or implants may pass. In the case of minimally invasive surgery (e.g., percutaneous surgery), the incision 209 may be as small as reasonably possible. Furthermore, the point of incision 209 may be located to avoid undue harm to the subject 102. For example, the point of incision 209 may be located at a threshold distance away from sensitive tissue or anatomical areas. In some cases, the point of incision 209 may be located to minimize the amount of tissue a surgical tool 210 must pass through during the surgery. In some examples, a cannula 207 is disposed in the sleeve 208. The cannula 207 may be tightly mated (e.g., with a clearance or interference fit) with the sleeve 208, preventing transverse movement of the cannula 207 within the sleeve 208. Furthermore, the cannula 207 may include a flange or collar near its proximal end, such that the cannula 207 may be inserted in the sleeve 208 until the flange/collar contacts the proximal end of the sleeve 208, thus preventing further longitudinal movement of the cannula 207. In other embodiments, the cannula 207 lacks a collar and is fully inserted within the sleeve 208. In these embodiments, further longitudinal movement of the cannula 207 is prevented by the friction fit between the cannula 207 and the sleeve 208. The cannula 207 may include a distal portion which protrudes beyond the sleeve 208. The distal portion may extend through the incision 209 of the subject 102 to a point within the body of the subject 102, e.g., to help reduce the chance of infection or other harm to the subject 102. The cannula 207 may include a hollow central tube 206 through which, e.g., surgical tools 210 may pass. The surgical tools 210 may be inserted from the proximal end of the cannula 207 and pass through the cannula 207 and the incision 209 into the body of the subject 102. As shown in FIG. 2A, a gap may remain between the distal end of the cannula 207 and bone tissue of the subject 102 when the sleeve 208 is disposed at a planned position and orientation. That is, the bone does not interfere with longitudinal positioning of the cannula 207, nor does the bone interfere with the orientation of the cannula 207.

Figure 2B:
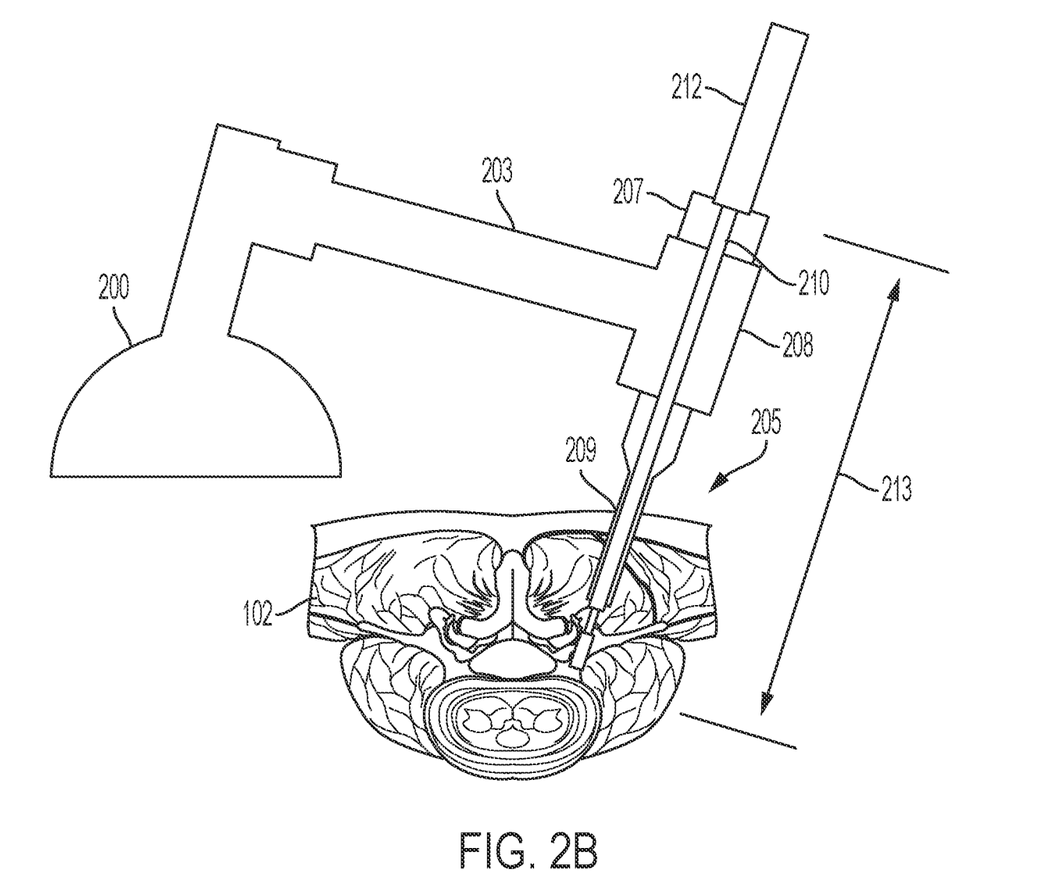

FIG. 2B, for example, shows an example surgical tool 210 inserted through the cannula 207 and into the body of the subject 102. Here, the proximal end of the surgical tool 210 includes a handle portion 212 that is wider than the hollow central tube 206. The handle portion 212 may serve as a depth stop, such that the surgical tool 210 can be inserted in the cannula 207 until the handle portion 212 contacts the cannula 207, the contact preventing further longitudinal movement of the surgical tool 210. In embodiments without a cannula 207, the surgical tool 210 can be inserted in the sleeve 208 until the handle portion 212 contacts the sleeve 208. In other embodiments, the surgical tool 210 may include a flange or collar which contacts the sleeve 208 or cannula 207 to prevent longitudinal movement of the surgical tool 210 past the point where the flange contacts, e.g., the proximal end of the guide sleeve 208. As shown in FIG. 2B, the position of the distal end of the surgical tool 210 is defined by the position and orientation of the sleeve 208 and the depth of insertion of the surgical tool 210 in the sleeve 208. In some embodiments, the surgical plan may include one or more desired positions of the distal end of the surgical tool 210. The surgical planning and execution system may determine one or more positions and orientations of the sleeve 208 to achieve the desired positions based on dimensions of the surgical tool 210. For example, the surgical planning and execution system may access a data store of known surgical tools 210. The data store may include dimensions of the surgical tool 210 (e.g., from CAD/CAM data files), including a longitudinal offset or distance 213 from the handle portion 212 (or collar/flange) of a surgical tool 210 (where the surgical tool 210 contacts the depth stop) to the distal tip of the surgical tool 210. The surgical planning and execution system may operate joints of the robotic system 200 to orient and position the sleeve 208 to achieve the desired position of the distal end of the surgical tool 210.

In some examples, the surgical planning and execution system positions and orients the sleeve 208 before the surgical tool 210 is inserted. The position and orientation of the sleeve 208 may define a longitudinal trajectory of the distal end of the surgical tool 210. As the surgical tool 210 is inserted in the sleeve 208 (or cannula 207), the distal end of the surgical tool 210 may follow the defined trajectory along the axis of the sleeve 208. The surgical tool 210 may be laterally constrained by the sleeve 208 as it follows the trajectory in a longitudinal direction defined by the orientation of the sleeve 208. For example, the surgical planning and execution system may define a maximum depth for tissue removal (e.g., by a tissue-removing tool 210 such as a drill or burr). The surgical planning and execution system may position and orient the sleeve 208 so that when the surgical tool 210 is fully inserted, the distal end achieves the maximum tissue-removal depth. Furthermore, the surgical planning and execution system may position and orient the sleeve 208 so that as the surgical tool 210 is inserted along the longitudinal axis of the sleeve 208, the distal end of the surgical tool 210 moves along the longitudinal axis to achieve the maximum tissue-removal depth. Thus, the surgical tool 210 may encounter (and, e.g., remove) tissue along the longitudinal axis of the sleeve 208 as the surgical tool 210 is being inserted. Because the sleeve 208 acts as a depth stop, the surgeon may fully insert the surgical tool 210 without the distal end of the surgical tool 210 passing beyond the maximum tissue-removal depth. This approach may be used, e.g., in facet decortication, removing tissue from a vertebra by inserting a surgical tool 210 having a burr end effector into the sleeve 208. Removing tissue from the vertebra along the configured trajectory, as the surgical tool 210 is plunged to the desired longitudinal position, may encourage spinal fusion. In some examples, the surgical planning and execution system positions and orients the sleeve 208 while the surgical tool 210 is inserted (and potentially operating). In the case of a subject 102 having a tumor, for example, the surgical planning and execution system may move or scan the distal end of a tissue-removing tool 210 through a three-dimensional volume to remove the tumor in much the same way a Computer Numerical Control (CNC) milling machine removes material during a manufacturing process. The three-dimensional volume may be determined by the surgical planning and execution system based, e.g., on received medical images and may be modified, as appropriate, during surgery, e.g., based on real-time sensor data. This approach may be suitable for performing continuous bone cutting or perforation, e.g., for laminectomy, facetectomy, craniotomy, etc.

Figure 2C:
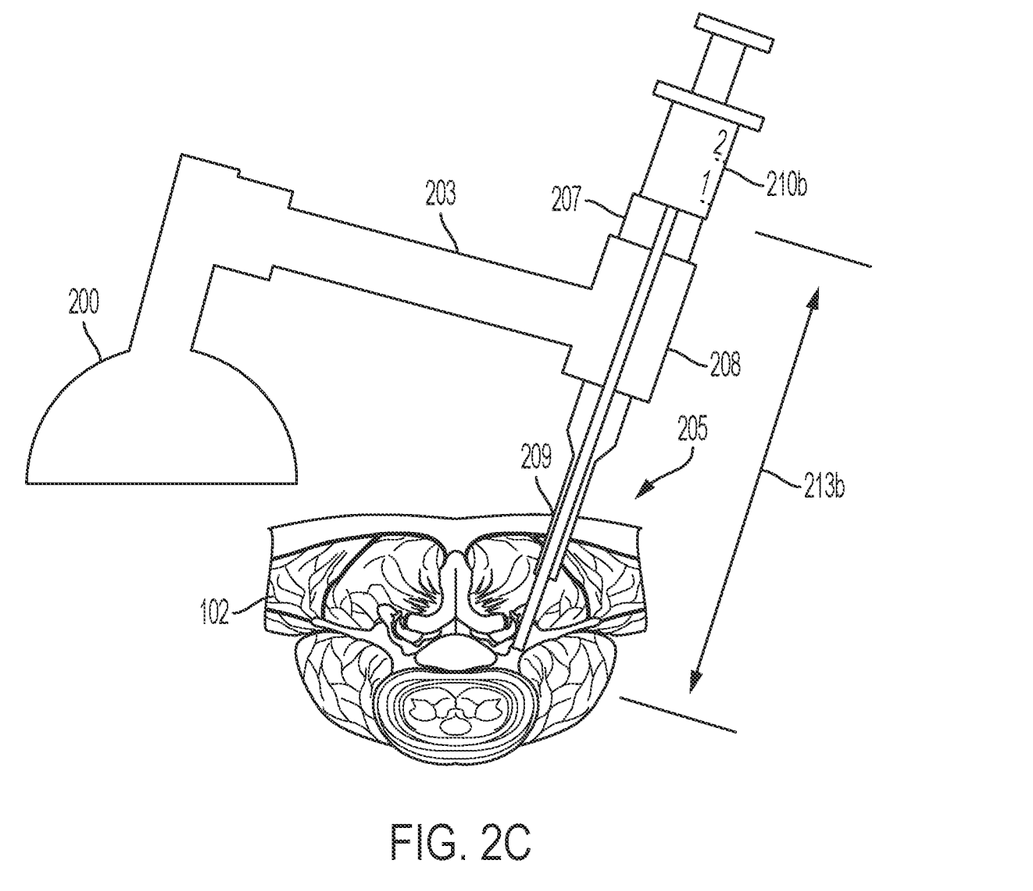

The surgical planning and execution system may monitor the position of the distal tip of the surgical tool 210 in real-time during surgery. Although the distal tip of the surgical tool 210 may not be visible from outside the body of the subject 102, the surgical planning and execution system may include an x-ray or other medical imaging system capable of displaying or monitoring the position of the surgical tool 210 and making the position known to the surgeon. The monitored position of the surgical tool 210 may be used to refine or recalibrate the surgical plan and/or refine the position and/or orientation of the sleeve 208. In some examples, the surgery may include multiple phases. For example, a spinal fusion surgery may include a first phase that includes removing some bone tissue, e.g., using a surgical tool 210 having a burr end effector. The surgery may include a subsequent phase that includes delivering bone graft or other material at the site of the bone tissue removal. That is, both the first phase and the subsequent phase target the same portion of the subject's anatomy. The bone graft may be delivered using a device including a syringe or other surgical tool 210 capable of accurately dispensing a volume of material. FIG. 2C, for example, shows the robotic system 200 after the previous (e.g., bone-tissue removing) tool 210 is replaced with a subsequent (bone-graft injecting) tool 210b. The subsequent tool 210b may have a subsequent offset or distance 213b between a wide portion of the surgical tool 210b (where the surgical tool 210b makes contact with the depth stop, preventing further longitudinal movement of the surgical tool 210b) and the distal end of the surgical tool 210b. The surgical planning and execution system may adjust the position and orientation of the sleeve 208 to accommodate the difference. As shown in FIG. 2C, the sleeve 208 has been slightly repositioned to accommodate the different length 213, but the orientation (longitudinal axis) has not been adjusted, nor has the point of incision 209. In this embodiment, the trajectory of the distal end of the subsequent tool 210b is the same as the trajectory of the distal end of the previous tool 210. In some examples, previous and subsequent tools (210, 210b) are designed to have similar distances (213, 213b) between their wide portion and their distal ends. In these examples, the surgical planning and execution system may not need to adjust the position of the sleeve 208.

Figure 2D:
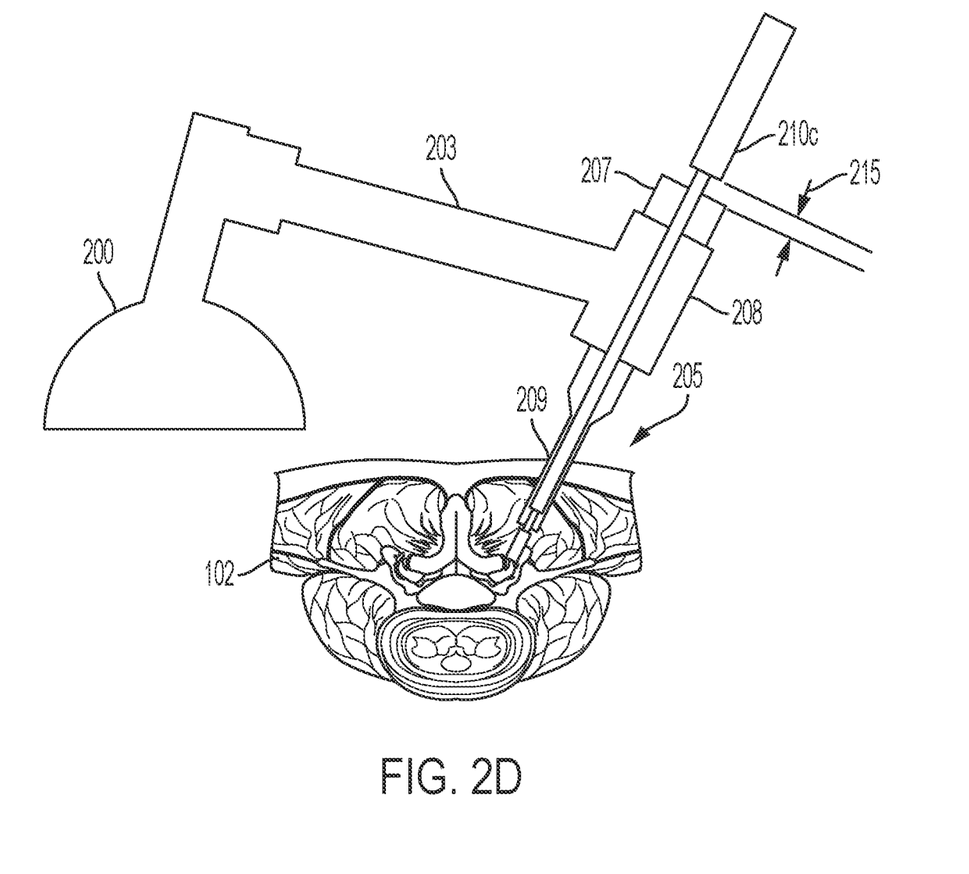

In some examples, the surgical planning and execution system positions and orients the sleeve 208 during a first phase of the surgery, then repositions and/or reorients the sleeve 208 during a subsequent phase of the surgery. For example, a spinal fusion surgery may include a preliminary phase that targets one portion of the vertebra, such as a facet, and a subsequent phase that targets a different portion of the vertebra, such as a pedicle. The first phase may include facet decortication, e.g., to promote fusion, and the second phase may include installing one or more implants, such as a pedicle screw. The surgical planning and execution system may reposition and/or reorient the sleeve 208 between the preliminary (e.g., facet decortication) and subsequent (e.g., implant installation) phases. In some examples, the surgical tool 210 is removed from the guide sleeve 208 between each phase. FIG. 2D shows the robotic system 200 after reconfiguration for a subsequent phase. As shown in FIG. 2D, the surgical planning and execution system has positioned and oriented the sleeve 208 to provide a different trajectory (along a different longitudinal axis) for tools 210 inserted in the sleeve 208. In some examples, the surgical planning and execution system configures the robotic system 200 to use the same incision point 209 through the fascia of the subject 102. Reusing the incision point 209 for subsequent phases of the surgery may further reduce the probability of infection or other negative outcome to the subject 102. Here, the distal end of a surgical tool 210 inserted into the sleeve 208 follows a new trajectory, through the incision point 209, targeting a pedicle of the vertebra, rather than a facet. The surgical planning and execution system may position the sleeve 208 so that a desired position of the distal end of a pedicle-screw implanting tool (e.g., 210c) is achieved. In some examples, during some phases of the surgery, the surgical planning and execution system positions the sleeve 208 based on the trajectory of the distal end of the surgical tool 210 rather than the position of the distal end. As shown in FIG. 2D, the trajectory of a pedicle-screw implanting tool 210c intersects a pedicle of a vertebra of the subject 102. In this embodiment, the distal end of the surgical tool 210c is not fully inserted in the sleeve 208 when the distal end of the surgical tool 210c is positioned at the pedicle. Because the head of a pedicle screw interacting with the pedicle limits the longitudinal movement of the pedicle screw, the surgical planning and execution system may be configured to deemphasize positioning the sleeve 208 to also act as a depth stop for the surgical tool 210c. Instead, the surgical tool 210c may be inserted relative to an axial reference of the guide sleeve 208. For example, the surgical tool 210c may be inserted until a flange of the surgical tool 210c is within a fixed distance 215 (e.g., 2 mm) of the proximal end of the guide sleeve 208. In other phases of the surgery, however, the surgical planning and execution system may emphasize positioning the sleeve 208 to act as a depth stop, e.g., when the distal end of a surgical tool 210 might contact a fragile or sensitive portion of the subject's anatomy.

Figure 3:
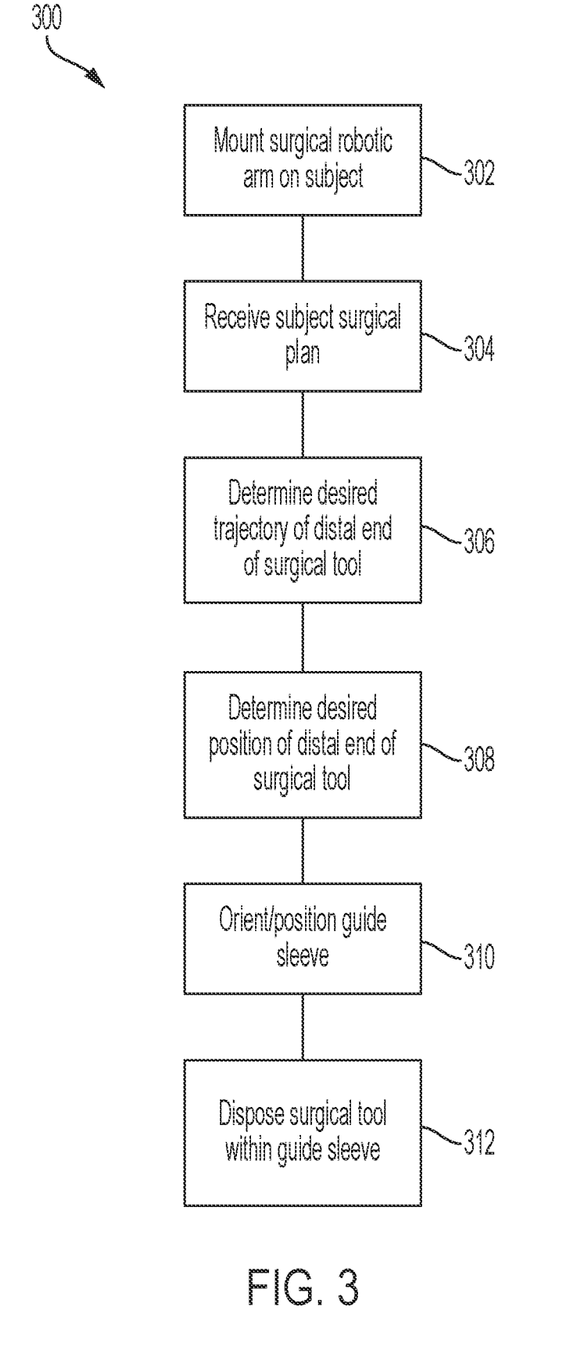
FIG. 3 is a flowchart of a method for positioning a surgical tool.

FIG. 3 shows a method 300 of positioning a surgical tool 210. At step 302, the method 300 includes mounting a surgical robotic arm 203 on a subject 102. As discussed above, the robotic arm 203 may include a guide sleeve 208 whose position defines axial and lateral directions. At step 304, the method 300 includes receiving, from an electronic device, a surgical plan associated with the subject 102. In some examples, the surgical plan includes three-dimensional preoperative data related to the subject 102, such as the pre-operative configuration of the spine of the subject 102. The preoperative data maybe used to register the position of the guide sleeve 208 with respect to the subject 102. At step 306, the method 300 includes determining, based on the surgical plan, a desired trajectory of the distal end of the surgical tool 210 as the surgical tool 210 is inserted into the guide sleeve 208. As the surgical tool 210 is inserted into the guide sleeve 208, the distal end of the surgical tool 210 follows the desired trajectory. In some examples, the surgical tool 210 removes tissue as it follows the trajectory. That is, the trajectory is determined based on tissue to be removed from the subject 102 during the surgery. At step 308, the method 300 includes determining, based on the surgical plan, a desired position of the distal end of the surgical tool 210. At step 310, the method 300 includes transmitting one or more control signals to the robotic arm 203, causing the robotic arm 203 to orient and position the guide sleeve 208 based on one or more dimensions of the surgical tool 210 and the desired trajectory and position of the distal end of the surgical tool 210. In some examples, the surgical tool 210 includes a flange (or similar structure) that defines the furthest extent the surgical tool 210 can be inserted into the guide sleeve 208. The method 300 may cause the robotic arm 203 to orient and position the guide sleeve 208 such that the distal end of the surgical tool 210 achieves the desired position when the surgical tool 210 is fully inserted in the guide sleeve 208, e.g., when the flange of the surgical tool 210 contacts the proximal end of the guide sleeve 208. At step 312, the method 300 includes disposing the surgical tool 210 within the guide sleeve 208 such that the lateral position of the surgical tool 210 is defined by the guide sleeve 208 and an axial position of a distal end of the surgical tool 210 is defined relative to an axial reference of the guide sleeve 208. In some examples, the axial reference is the proximal end of the guide sleeve 208.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 4:
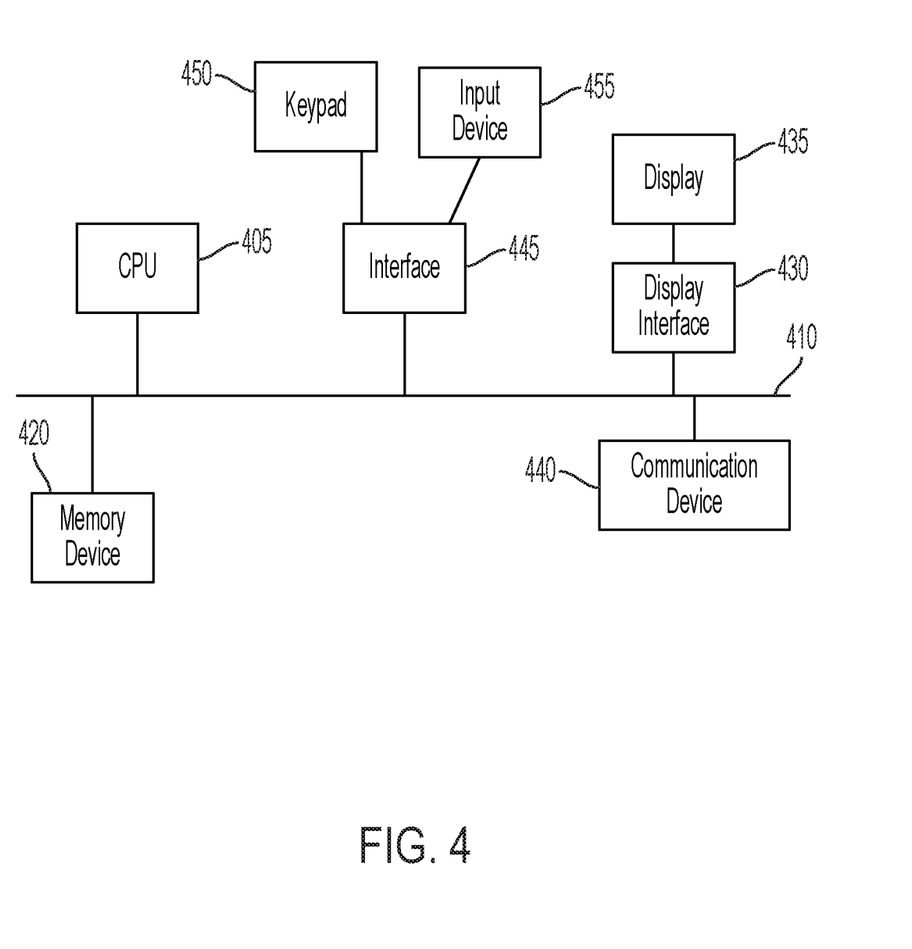
FIG. 4 shows a block diagram of an example of internal hardware that may be used to contain or implement program instructions according to an embodiment.

FIG. 4 illustrates example hardware that may be used to contain or implement program instructions. A bus 410 serves as the main information highway interconnecting the other illustrated components of the hardware. Central Processing Unit (CPU) 405 is the central processing unit of the system, performing calculations and logic operations required to execute a program. CPU 405, alone or in conjunction with one or more of the other elements disclosed in FIG. 4, is an example of a processor as such term is used within this disclosure. Read only memory (ROM) and random-access memory (RAM) constitute examples of non-transitory computer-readable storage media 420, memory devices or data stores as such terms are used within this disclosure.

Program instructions, software or interactive modules for providing the interface and performing any querying or analysis associated with one or more data sets may be stored in the memory device 420. Optionally, the program instructions may be stored on a tangible, non-transitory computer-readable medium such as a compact disk, a digital disk, flash memory, a memory card, a universal serial bus (USB) drive, an optical disc storage medium and/or other recording medium.

An optional display interface 430 may permit information from the bus 410 to be displayed on the display 435 in audio, visual, graphic or alphanumeric format. Communication with external devices may occur using various communication ports 440. A communication port 440 may be attached to a communications network, such as the Internet or an intranet.

The hardware may also include an interface 445 which allows for receipt of data from input devices such as a keypad 450 or other input device 455 such as a touch screen, a remote control, a pointing device, a video input device and/or an audio input device.

It will be appreciated that the various above-disclosed and other features and functions, or alternatives thereof, may be desirably combined into many other different systems or applications or combinations of systems and applications. Also, that various presently unforeseen or unanticipated alternatives, modifications, variations or improvements therein may be subsequently made by those skilled in the art which are also intended to be encompassed by the following claims.

What is claimed is:

1. A system for positioning a surgical tool, the system comprising:
 a surgical robotic system comprising a robot arm, the robot arm comprising a guide sleeve, the guide sleeve defining axial and lateral directions;
 one or more computer readable storage devices configured to store a plurality of computer executable instructions; and
 one or more hardware computer processors in communication with the one or more computer readable storage devices and configured to execute the plurality of computer executable instructions, causing the system to:
  receive a surgical plan associated with a subject, the surgical plan comprising three-dimensional preoperative data related to the subject;
  determine, based on the surgical plan, a desired trajectory of a distal end of the surgical tool as the surgical tool is inserted into the guide sleeve;
  determine, based on the surgical plan, a desired position of the distal end of the surgical tool;
  transmit one or more control signals to the surgical robotic system, causing the surgical robotic system to orient and position the guide sleeve based on one or more dimensions of the surgical tool and the desired trajectory and position of the distal end of the surgical tool, such that the distal end of the surgical tool follows the desired trajectory when the surgical tool is inserted in the guide sleeve, and such that the distal end of the surgical tool achieves the desired position when the surgical tool is fully inserted in the guide sleeve;
  determine, based on the surgical plan, a second desired trajectory of a distal end of a second surgical tool as the second surgical tool is inserted into the guide sleeve;
  determine, based on the surgical plan, a second desired position of the distal end of the second surgical tool; and
  transmit one or more second control signals to the surgical robotic system, causing the surgical robotic system to reorient and/or reposition the guide sleeve based on one or more second dimensions of the second surgical tool and the second desired trajectory and position, such that the distal end of the second surgical tool follows the second desired trajectory when the second surgical tool is inserted in the guide sleeve, replacing the surgical instrument, and such that the distal end of the second surgical tool achieves the second desired position when the second surgical tool is fully inserted in the guide sleeve.

2. The system of claim 1, wherein the plurality of computer executable instructions, when executed, further cause the system to transmit one or more second control signals to the surgical robotic system, causing the surgical robotic system to orient and position the guide sleeve based on one or more second dimensions of the second surgical tool.

3. The system of claim 2, wherein the surgical tool is a burr and the second surgical tool is a bone graft delivery device.

4. The system of claim 1, wherein the desired trajectory and the second desired trajectory are different.

5. The system of claim 4, wherein the desired trajectory and the second desired trajectory pass through the fascia of the subject at the same point.

6. The system of claim 1, wherein the plurality of computer executable instructions, when executed, further cause the system to:
 determine, based on the surgical plan, a plurality of additional desired positions of the distal end of the surgical tool, the plurality of additional desired positions defining a volume; and
 transmit one or more additional control signals to the surgical robotic system, causing the surgical robotic system to orient and position the guide sleeve based on the one or more dimensions of the surgical tool and the plurality of additional desired positions of the distal end of the surgical tool, such that when the surgical tool is fully inserted in the guide sleeve, the distal end of the surgical tool achieves the plurality of additional desired positions.

7. The system of claim 1, wherein the robot arm further comprises a cannula disposed within the guide sleeve, wherein the cannula is configured to receive the surgical tool.

8. The system of claim 1, wherein the surgical tool comprises a flange; and
wherein the guide sleeve is configured to prevent the surgical tool from being inserted into the guide sleeve past the point where the flange contacts the proximal end of the guide sleeve.

9. A robotic system comprising:
a robot arm comprising a guide sleeve, the guide sleeve defining axial and lateral directions; and
a surgical planning and execution system configured to:
determine a desired trajectory of a distal end of a surgical tool as the surgical tool is inserted into the guide sleeve;
determine one or more dimensions of the surgical tool;
determine a desired position of the distal end of the surgical tool;
cause the robot arm to orient and position the guide sleeve based on the one or more dimensions of the surgical tool and the desired trajectory and position of the distal end of the surgical tool, such that the distal end of the surgical tool follows the desired trajectory when the surgical tool is inserted in the guide sleeve, and such that the distal end of the surgical tool achieves the desired position when the surgical tool is fully inserted in the guide sleeve;
determine a second desired trajectory of a distal end of a second surgical tool as the second surgical tool is inserted into the guide sleeve;
determine one or more dimensions of the second surgical tool;
determine a desired position of the distal end of the second surgical tool; and
cause the robot arm to reorient and/or reposition the guide sleeve based on the one or more dimensions of the second surgical tool and the desired trajectory and position of the distal end of the second surgical tool, such that the distal end of the second surgical tool follows the second desired trajectory when the second surgical tool is inserted in the guide sleeve, replacing the surgical instrument, and such that the distal end of the second surgical tool achieves the desired position when the second surgical tool is fully inserted in the guide sleeve.

10. The robotic system of claim 9, wherein the robot arm further comprises a cannula disposed within the guide sleeve, wherein the cannula is configured to receive the surgical tool.

11. The robotic system of claim 9, wherein the surgical tool comprises a drill or burr.

12. A method of positioning a surgical tool, the method comprising:
providing a surgical robotic arm including a guide sleeve, the guide sleeve defining axial and lateral directions;
receiving, from an electronic device, a surgical plan associated with a subject, the surgical plan comprising three-dimensional preoperative data related to the subject;
determining, based on the surgical plan, a desired trajectory of a distal end of the surgical tool as the surgical tool is inserted into the guide sleeve;
determining, based on the surgical plan, a desired position of the distal end of the surgical tool;
transmitting one or more control signals to the robotic arm, causing the robotic arm to orient and position the guide sleeve based on one or more dimensions of the surgical tool and the desired trajectory and position of the distal end of the surgical tool, such that the distal end of the surgical tool follows the desired trajectory when the surgical tool is inserted in the guide sleeve, and such that the distal end of the surgical tool achieves the desired position when the surgical tool is fully inserted in the guide sleeve;
disposing the surgical tool within the guide sleeve such that the lateral position of the surgical tool is defined by the guide sleeve and an axial position of a distal end of the surgical tool is defined relative to an axial reference of the guide sleeve;
removing the surgical tool from the guide sleeve;
determining, based on the surgical plan, a second desired trajectory of a distal end of a second surgical tool as the second surgical tool is inserted into the guide sleeve;
after removing the surgical tool, repositioning and/or reorienting the guide sleeve based on the second desired trajectory; and
after repositioning and/or reorienting the guide sleeve, disposing the second surgical tool within the guide sleeve, replacing the surgical instrument.

13. The method of claim 12, wherein:
the axial reference is the proximal end of the guide sleeve; and
the proximal end of the guide sleeve comprises a depth stop.

14. The method of claim 12, wherein the desired position is internal to the subject and the axial reference is external to the subject.

15. The method of claim 12,
wherein the desired trajectory of the distal end of the surgical tool targets a facet joint of a vertebra of the subject; and
wherein the second desired trajectory of the distal end of the second surgical tool targets a pedicle of the vertebra of the subject.

16. The method of claim 12, further comprising monitoring the position of the distal end of the surgical tool with a medical imaging system while disposing the surgical tool in the guide sleeve.

17. The method of claim 12, further comprising:
receiving three-dimensional preoperative data related to the subject, and
registering the subject position and orientation relative to the robotic arm based on the preoperative data.

* * * * *